United States Patent [19]

Galbo et al.

[11] Patent Number: 5,015,683
[45] Date of Patent: May 14, 1991

[54] BIS(1-HYDROCARBYLOXY-2,2,6,6-TETRAMETHYLPIPERIDIN-4-YL)-AMINE DERIVATIVES AND STABILIZED COMPOSITIONS

[75] Inventors: James P. Galbo, Hartsdale; Ramanathan Ravichandran, Nanuet, both of N.Y.

[73] Assignee: Ciba-Geigy Corporation, Ardsley, N.Y.

[21] Appl. No.: 479,909

[22] Filed: Feb. 14, 1990

Related U.S. Application Data

[63] Continuation-in-part of Ser. No. 326,849, Mar. 21, 1989, abandoned.

[51] Int. Cl.$^5$ .................. C08K 5/3435; C07D 211/00
[52] U.S. Cl. ..................................... 524/103; 546/186
[58] Field of Search .................. 524/91, 95, 102, 103; 546/186

[56] References Cited

U.S. PATENT DOCUMENTS

| | | | |
|---|---|---|---|
| 3,993,655 | 11/1976 | Rasberger et al. | 524/99 |
| 4,198,334 | 4/1980 | Rasberger | 524/99 |
| 4,344,876 | 8/1982 | Berner | 524/91 |
| 4,665,185 | 5/1987 | Winter et al. | 546/184 |
| 4,780,493 | 10/1988 | Cantatore et al. | 524/99 |
| 4,851,461 | 7/1989 | Nelson et al. | 524/99 |

OTHER PUBLICATIONS

Shlyanpintokh et al, "Developments in Polymer Stabilization", V 41-70 (1982).

*Primary Examiner*—Kriellion Morgan
*Attorney, Agent, or Firm*—Luther A. R. Hall

[57] ABSTRACT

Compounds derived from bis(1-hydrocarbyloxy-2,2,6,6-tetramethylpiperidin-4-yl)amine are effective stabilizers in preventing the degradation of polymers subject to the deleterious effects of actinic light.

23 Claims, No Drawings

BIS(1-HYDROCARBYLOXY-2,2,6,6-TETRAME-THYLPIPERIDIN-4-YL)-AMINE DERIVATIVES AND STABILIZED COMPOSITIONS

This is a continuation-in-part of application Ser. No. 326,849, filed on Mar. 21, 1989 now abandoned.

The instant compounds are derivatives of bis(1-hydrocarbyloxy hindered amine)amine which are effective stabilizers for protecting polymers from the adverse effects of actinic light.

The instant compounds have structures different from the 1-hydrocarbyloxy derivatives described in copending patent application Ser. No. 259,950 pending.

DETAILED DISCLOSURE

The instant invention pertains to compounds having the formula

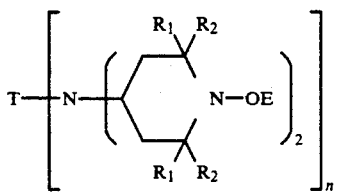

wherein
n is 1 to 4,
$R_1$ and $R_2$ are independently alkyl of 1 to 4 carbon atoms or together $R_1$ and $R_2$ are pentamethylene,
E is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl, and T is a radical of valence n, where, when n is 1, T is hydrogen, alkanoyl of 2 to 20 carbon atoms, cycloalkanoyl of 6 to 13 carbon atoms, aroyl of 7 to 11 carbon atoms, aralkanoyl of 8 to 16 carbon atoms, substituted carbamoyl or alkoxycarbonyl of 2 to 20 carbon atoms, when n is 2, T is —CO—, a divalent acyl radical of an aliphatic, cycloaliphatic, araliphatic or aromatic dicarboxylic acid, a divalent acyl radical of a dicarbamic acid or a divalent acyl radical of a mixed carboxylic-carbamic acid, when n is 3, T is a trivalent acyl radical of an aliphatic, cycloaliphatic, araliphatic or aromatic tricarboxylic acid, when n is 4, T is a tetravalent acyl radical of an aliphatic, cycloaliphatic or aromatic tetracarboxylic acid.

Preferably n is 2 to 4.

$R_1$ and $R_2$ are preferably each methyl.

E is preferably alkyl of 1 to 12 carbon atoms, cyclohexyl or alpha-methylbenzyl. Most preferably E is methyl, heptyl, octyl, nonyl or cyclohexyl.

When n is 2, T is preferably alkanedioyl of 2 to 10 carbon atoms or hexamethylenedicarbamoyl, most preferably oxalyl, succinyl or sebacoyl.

When n is 4, T is preferably 1,2,3,4-butanetetracarboxoyl, 1,2,3,4-but-2-enetetracarboxoyl, 1,2,3,5-pentanetetracarboxoyl or 1,2,4,5-pentanetetracarboxoyl; most preferably 1,2,3,4-butanetetracarboxoyl.

SYNTHESIS

N-Methoxy piperidine derivatives are synthesized by the reaction of an appropriate N-oxyl precursor with methyl radicals generated by the thermolysis of di-tert-butyl peroxide in an inert solvent such as chlorobenzene as seen in copending patent application Ser. No. 259,950.

U.S. Pat. No. 4,665,185 teaches the preparation of N-hydroxypiperidines by oxidation of the hindered amine with a hydroperoxide and metal oxide catalyst followed by catalytic hydrogenation. The N-hydroxypiperidines by oxidation of the hindered amine with a hydroperoxide and metal oxide catalyst followed by catalytic hydrogenation, the N-hydroxy compounds are alkylated by reaction with sodium hydride and an alkyl iodide.

The preferred method of making the N-hydrocarbyl compounds involves the thermal reaction of a hydrocarbon solution, especially effective with hydrocarbons such as cyclohexane, heptane, octane, nonane or ethylbenzene, of the hindered amine or its N-oxyl derivative with tert-butyl hydroperoxide and a metal oxide catalyst. See copending patent application Ser. Nos. 259,949 and 259,950.

The instant compounds are prepared by two general synthetic routes. Bis(2,2,6,6-tetramethylpiperidin-4-yl)-amine is reacted with an acid chloride or an isocyanate and the N-hydrocarbyloxy group is introduced by the preferred method described supra.

Alternatively, the N-hydrocarbyloxy moiety can be introduced first, followed by reaction with an acid chloride or isocyanate. Bis(1-hydrocarbyloxy-2,2,6,6-tetramethylpiperidin-4-yl)amines are prepared by reductive amination of 4-oxo-1-hydrocarbyloxy piperidines with 4-amino-1-hydrocarbyloxy piperidines.

The intermediates useful in preparing the instant compounds are largely items of commerce.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

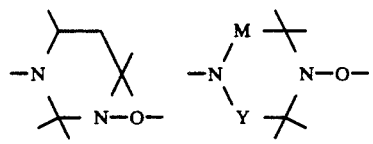

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentne or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α, β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl-butyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1, 4-dimethylol-cyclohexane terephthalate, poly-[2,2-(4-hydroxyphenyl)-proplane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene-/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenol-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenol)-propionic acid with monohydric or polyhydric alcohols, for example

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenol)-propionic acid with monohydric or polyhydric alcohols, for example

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid |

-continued diamide 1.9. Amides of β-(3,5-di-tert-butyl-4-hydroxyphenol)-propionic acid for example
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles, for example
5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxyl-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyano-vinyl)-2-methyl-indoline.

2.5 Nickel compounds, for example nickel complexes of 2,2'-thio-bis-[4-(1,1,3,3-tetramethylbutyl)-phenol], such as the 1:1 or 1.2 complex, optionally with additional ligands such as n-butylamine, triethanolamine or N-cyclo-hexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tertabutyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert-butyl-oxanilide, 2-ethoxyl-2'-ethyl-oxanilide, N,N'-bis-(3-dimethylaminopropyl)-oxalamide, 2-ethyoxy-5-tert-butyl-2'-ethyloxanilide and its mixture with 2-ethoxy-2'ethyl-5,4'-di-tert-butyloxanilide and mixtures of ortho- and para-methoxy-as well as of o- and p-ethoxy-disubstituted oxanilides.

2.8. Hydroxylphenyl-s-triazines, for example 2,6-bis-(2,4-dimethylphenyl)-4-(2-hydroxy-4-octyloxyphenyl-s-triazine; 2,6-bis-(2,4-dimethlphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4(2-hydroxyethoxy)phenyl]-6-phenyl-s-triazine; 2,4-bis[2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen with N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972, "Lackkunstharze" (1977, by H. Wagner and H. F. Sarx, on pages 299–238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/ melamine resins and alkyd/acrylic/melamine resins (see H. Wagner and H. F. Sarx, op. cit., pages 99–123. Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anyhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are referenced in a paper by H. J. Heller in European Polymer Journal Supplement, 1969, pp 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyl-oxy-, 4-benzyloxy; 4,2',4'-trihydroxy- and 2'-hydroxy-4,4'-dimethoxy derivatives.

(c) Acrylates, for example, alpha-cyano-$\beta,\beta$-diphenyl-acrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alpha-carbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclo-hexyl-diethanolamine, nickel dibutyldithiocarbamate, nickel salts of 4-hydroxy-3,5-di-tert-butylbenzylphosphonic acid monalkyl esters, such as of the methyl, ethyl or butyl ester, nickel complexes of ketoximes such as of 2-hydroxyl-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyl-oxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha, alpha-dimethylbenzyl)-phenyl]-2H-benzotriazole, 2-(2-hydroxy-3,5-di-tert-octylphenyl)-2H-benzotriazole, 2-(2-hydroxy-3-alpha, alpha-dimethylbenzyl-5-tert-octyl-phenyl)-2H-benzotriazole, 2-(2-hydroxy-3-tert-octyl-5-alpha, alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole dodecylated 2-(2-hydroxy-5-methylphenyl)-2H-benzotriazole, 2-[2-hydroxyl-3-tert-butyl-5-(2-octyloxy-carbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha, alphadimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyl-oxycarbonyl)ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising (a) an acid catalyzed thermoset coating or enamel based on hot, crosslinkable acrylic, polyester or alkyd resins, (b) a NOE -substituted 2,2,6,6-tetraalkylpiperidine compound, and (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-di-tert.butylphenyl)pentaerythritol disphosphite, tristearyl-sorbitol triphosphite, tetrakis-(2,4-di-tert.butylphenyl)-4,4'-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are present for the purpose of illustration only and are not to be construed to limit the nature or scope of the instant invention in any manner whatsoever.

EXAMPLE 1

N,N,N',N'-Tetrakis(1-octyloxy-2,2,6,6-tetramethylpiperidin-4-yl)sebacamide

A mixture of 68.0 grams (528 mmol) of 70% aqueous tert-butyl hydroperoxide, 225 ml of n-octane, and 10 grams of sodium chloride is agitated in a separatory funnel. The organic phase is isolated. On-half of the tert-butyl hydroperoxide/n-octane solution is added to 25.0 grams (33 mmol) of N,N,N',N'-tetrakis(2,2,6,6-tetramethylpiperidin-4-yl)sebacamide and 0.3 gram of molybdenum trioxide. The mixture is heated at reflux for one hour. Water is collected in a Dean-Stark trap. The remainder of the tert-butyl hydroperoxide/n-octane solution is then added to the refluxing red reaction mixture over a two-hour period. The mixture is heated at reflux for another four hours after the addition is complete in order to discharge the red color. Solids are removed by filtration, and the filtrate is evaporated under reduced pressure. The crude product is passed through a short silica gel column with 4:1 heptane:ethyl acetate as the eluent to afford 22.2 grams (53% yield) of the title compound as a glass.

Analysis: Calcd for $C_{78}H_{152}N_6O_6$: C, 73.8; H, 12.1; N, 6.6. Found: C, 73.8; H, 12.1, N, 6.5.

EXAMPLE 2

N,N,N',N'-Tetrakis(1-cyclohexyloxy-2,2,6,6-tetramethylpiperidine-4-yl)sebacamide A mixture of 35.0 grams (46 mmol) of N,N,N',N'-tetra-kis(2,2,6,6-tetramethylpiperidine-4-yl)sebacamide, 74.0 grams (739 mmol) of 90% tert-butyl hydroperoxide, 0.4 gram of molybdenum trioxide, and 250 ml of cyclohexane is heated at 140°–150° C. for five hours in a Fischer-Porter pressure bottle. The red reaction mixture is treated with 19.0 grams of fresh 90% tert-butyl hydroperoxide, 0.2 grams of molybdenum trioxide, and 50 ml of cyclohexane. The mixture is then heated at 150° C. for three hours to discharge the red color. Solids are removed by filtration, and the filtrate is evaporated at reduced pressure. The residue is passed through silica gel with 4:1 heptane:ethylacetate as the eluent to afford 28.3 grams (53% yield) of the title compound as a white solid melting at 129°–133° C.

Analysis: Calcd for $C_{70}H_{128}N_6O_6$: C, 73.1; H, 11.2; N, 7.3. Found: C, 72.7; H, 11.6; N, 7.3.

EXAMPLE 3

N,N,N',N'-Tetrakis(1-cyclohexyloxy-2,2,6,6-tetramethylpiperidin-4yl-succinamide

A mixture of 7.5 grams (11 mmol) of N,N,N',N'-tetrakis (2,2,6,6-tetramethylpiperidin-4-yl)succinamide, 22.3 g grams (223 mmol) of 90% tert-butyl hydroperoxide, 0.15 gram of molybdenum trioxide and 100 ml of cyclohexane is heated at 150°–160° C. for five hours in a Fischer-Porter pressure bottle. The orange mixture is then treated with 7.0 grams of fresh 90% tert-butyl hydroperoxide, 0.1 gram of molybdenum trioxide, and 40 ml of cyclohexane. The reaction mixture is heated at 150°–160° C. for three hours to discharge the red color. The reaction mixture is diluted with 200 ml of chloroform and filtered. The filtrate is evaporated under reduced pressure to obtain a solid which is dissolved in warm methylene chloride. The methylene chloride solution is filtered and slowly evaporated while isopropyl alcohol is added to induce crystallization of the product. The title compound is obtained as a white solid, which melts at 281°–282° C. with decomposition, in a yield of 8.3 grams (70% yield).

Analysis: Calcd for $C_{64}H_{116}N_6O_6$: C, 72.1; H, 11.0; N, 7.9. Found: C, 71.7; H, 11.0; N, 7.8.

EXAMPLE 4

N,N,N'N'-Tetrakis(1-cyclohexyloxy-2,2,6,6-tetramethylpiperidin-4-yl)oxamide

An anhydrous solution of tert-butyl hydroperoxide in cyclohexane is prepared by agitating a mixture of 32.3 grams (251 mmol) of 70% aqueous tert-butyl hydroperoxide, 150 ml of cyclohexane and 100 ml of saturated sodium chloride solution in a separatory funnel, separating the layers, and drying the organic layer over anhydrous magnesium sulfate. A mixture of 8.1 grams (12.6 mmol) of N,N,N',N'-tetrakis-(2,2,6,6-tetramethylpiperidin-4-yl)oxamide, 0.3 gram of molybdenum trioxide, and the previous prepared anhydrous tert-butyl hydroperoxide/cyclohexane solution is heated for three hours in a Fischer-Porter pressure bottle (bath temperature 150°–160° C.). Solids are removed by filtration, and the filtrate is evaporated under reduced pressure to obtain a solid. Recrystallization from 2:1 isopropyl alcohol:methylene chloride affords 9.8 grams (75% yield) of the title compound as a white solid melting at 278° C. with decomposition.

Analysis: Calcd for $C_{62}H_{112}N_6O_6$: C, 71.8; H, 10.9; N, 8.1. Found: C, 71.3; H, 10.6; N, 7.9.

EXAMPLE 5

N,N,N',N'-Tetrakis(1-octyloxy-2,2,6,6-tetramethylpiperidin-4-yl)oxamide

The title compound is prepared from N,N,N',N'-tetra-kis(2,2,6,6-tetramethylpiperidin-4-yl)oxamide and n-octane according to the procedure of Example 4.

EXAMPLE 6

N,N'-Bis[di(1-octyloxy-2,2,6,6-tetramethylpiperidin-4-yl)aminocarbonyl]-1,6-hexanediamine The title compound is prepared by the reaction of bis(1-octyloxy-2,2,6,6-tetramethylpiperidin-4-yl)amine with hexamethylene diisocyanate.

EXAMPLE 7

1-[N,N-Di(1-octyloxy-2,2,6,6-tetramethylpiperidin-4-yl)-ureido-methyl]-5-[N,N-di(1-octyloxy-2, 2,6,6-tetramethylpiperidin-4-yl)ureido]-1,3,3-trimethylcyclohexane The title compound is prepared by the reaction of bis(1-octyloxy-2,2,6,6-tetramethylpiperidin-4-yl)amine with 5-isocyanato-1-(isocyanatomethyl)-1,3,3-trimethylcyclohexane (or isophorone diisocyanate).

EXAMPLE 8

N',N''-1,6-hexanediyl-N,N,N''',N'''-tetrakis(1-cyclohexyloxy-2,2,6,6-tetramethylpiperidin-4-yl)bisurea A solution of 3.5 grams (20.8 mmol) of hexamethylene diisocyanate in 30 ml of methylene chloride is added over a 10-minute interval to a solution of 11.7 grams (23.7 mmol) of bis(1-cyclohexyloxy-2,2,6,6-tetramethylpiperidin-4-yl)amine in 50 ml of methylene chloride. The reaction mixture is then heated at reflux for 30 minutes. Solvent is evaporated and the residue is purified by flash chromatography on silica gel (2:1, heptane:ethyl acetate) followed by crystallization from methylene chloride:methanol to afford 6.9 grams (51% yield) of the title compound as a white solid melting at 138°–141° C.

Analysis: Calcd for $C_{68}H_{126}N_8O_6 \cdot H_2O$: C, 69.8; H, 11.0; N, 9.6. Found: C, 69.8; H, 10.8; N, 9.2.

EXAMPLE 9

Light Stabilization of Polyproylene

This example illustrates the light stabilizing effectiveness of instant stabilizers.

Polypropylene powder (Himont Profax 6501) stabilized with 0.2% by weight of n-octadecyl 3,5-di-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250ZC and 175 psi (1.2 ×10⁶ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by weight) | FS/BL Test Results (hours to Failure) |
|---|---|---|
| Control* | — | 340 |
| Example 1 | 0.1 | 1160 |

*Base resin plus 0.1% calcium stearate and 0.2% of n-octadecyl 3,5-di-tert-butyl-4-hydroxyhydrocinnamate.

EXAMPLE 10

A basecoat/clearcoat enamel is prepared by spray applying a 1.8-2.0 mile thick film of commercially available high solids thermoset acrylic melamine clearcoat over a 0.6-0.8 mil thick film of commercially available silver metallic basecoat (wet on wet) over 4 inch ×12 inch (10.16 cm ×30.48 cm) panels (Uniprime available from Advanced Coating Technology). The coated panels are then baked at 250° F. (121° C.) for 30 minutes. After storage for one week in an air-conditioned room, the coated panels are weathered in a QUV exposure apparatus according to ASTM G-53/77 using FS-40 bulbs. The 20° gloss is measured after periods of QUV exposure with the results given below.

| | 20° Gloss after Hours of QUV Exposure | | |
|---|---|---|---|
| Stabilizer (% by wt) | 0 | 1713 | 2632 |
| Unstabilized* | 94 | 9*** | — |
| 3% UVA** | 96 | 87 | 31 |
| 3% UVA plus 2% of Compound of Example 1 | 94 | 90 | 87 |
| 3% UVA plus 2% of Compound of Example 2 | 96 | 89 | 85 |

*No stabilizer is either basecoat or clearcoat.
**UVA is 2-[2-hydroxy-3-tert-butyl-5-(2-omega-hydroxy-octa-(ethyleneoxy)carbonyl)-ethylphenyl]-2H-benzotriazole.
***indicates cracking

EXAMPLE 11

A commercial white acrylic polyurethane refinish enamel is stabilized with 2% UV absorber and 2% of an instant compound (% by weight based on total resin solids). This material is spray applied to a thickness of 2.4-2.6 mil onto steel panels primed with a commercial epoxy-amine primer. After storage for one month in an air-conditioned room, the coated panels are weathered in a Xenon Arc Weatherometer. 20° Gloss values are measured after periods of Xenon Arc Weatherometer exposure with the results given below.

| | 20° Gloss after Hours of Xenon Arc Weatherometer Exposure | | |
|---|---|---|---|
| Stabilizer (% by wt) | 0 | 1845 | 3085 |
| Unstabilized | 85 | 52 | 30 |
| 2% UVA* plus 2% of Compound of Example 1 | 86 | 82 | 74 |

*UVA is 2-[2-hydroxy-3-tert-butyl-5-(2-omega-hydroxy-octa-(ethyleneoxy)carbonyl)-ethylphenyl]-2H-benzotriazole.

What is claimed is:
1. A compound having the formula

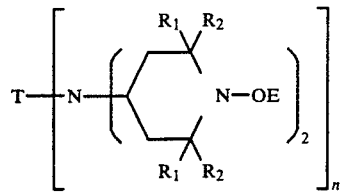

wherein
N is 1 to 4,
R₁ and R₂ are independently alkyl of 1 to 4 carbon atoms or together R₁ and R₂ are pentamethylene,
E is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bycyclic or tricyclic hydrocarbon of 7 to 12 carbon atoms or aryl of 6 to 10 carbon atoms or said aryl substituted by alkyl, and
T is a radical of valence n, where, when n is 1, T is hydrogen, alkanoyl of 2 to 20 carbon atoms, cycloalkanoyl of 6 to 13 carbon atoms, aroyl of 7 to 11 carbon atoms, aralkanoyl of 8 to 16 carbon atoms, carbamoyl or alkoxycarbonyl of 2 to 20 carbon atoms.
when n is 2, T is —CO—, a divalent acyl radical of an aliphatic, cycloaliphatic, araliphatic or aromatic dicarboxylic acid, a divalent acyl radical of a dicarbamic acid or a divalent acyl radical of a mixed carboxylic-carbamic acid,
when n is 3, T is a trivalent acyl radical of an aliphatic, cycloaliphatic, araliphatic or aromatic tricarboxylic acid, and
when n is 4, T is a tetravalent acyl radical of an aliphatic, cycloaliphatic or aromatic tetracarboxylic acid.
2. A compound according to claim 1 wherein n is 2 to 4.
3. A compound according to claim 2 wherein n is 2 or 4.
4. A compound according to claim 1 wherein R₁ and R₂ are each methyl.
5. A compound according to claim 1 where E is alkyl of 1 to 12 carbon atoms, cyclohexyl or alpha-methylbenzyl.
6. A compound according to claim 5 wherein E is methyl, heptyl, octyl, nonyl or cyclohexyl.
7. A compound according to claim 1 wherein, when n is 2, T is alkanedioyl or 2 to 10 carbon atoms or hexamethylenedicarbamoyl.
8. A compound according to claim 7 wherein T is oxalyl, succinyl or sebacoyl.
9. A compound according to claim 1 wherein, when n is 4, T is 1,2,3,4-butanetetracarboxoyl, 1,2,3,4-but-2-enetetracarboxoyl, 1,2,3,5-pentanetetracarboxoyl or 1,2,4,5-pentanetetracarboxoyl.
10. A compound according to claim 9 wherein T is 1,2,3,4-butanetetracarboxoyl.
11. The compound according to claim 1 which is N,N,N',N'-tetrakis(1-octyloxy-2,2,6,6-tetramethyl-piperidin-4-yl)sebacamide.
12. The compound according to claim 1 which is N,N,N',N'-tetrakis(1-cyclohexyloxy-2,2,6,6-tetramethylpiperidine-4-yl)sebacamide.

13. The compound according to claim 1 which is N,N,N',N'-tetrakis(1-cyclohexyloxy-2,2,6,6-tetramethylpiperidin-4-yl)succinamide.

14. The compound according to claim 1 which is N,N,N',N'-tetrakis(1-cyclohexyloxy-2,2,6,6-tetramethylpiperidin-4-yl)oxamide.

15. The compound according to claim 1 which is N',N''-1,6-hexanediyl-N,N,N'''-tetrakis(1-cyclohexyloxy-2,2,6, 6-tetramethylpiperidin-4-yl)bisurea.

16. A composition stabilized against the deleterious effects of actinic light which comprises
    (a) a polymer subject to the deleterious effects of actinic light, and
    (b) an effective stabilizing amount of a compound according to claim 1.

17. A composition according to claim 16 wherein the polymer is a polyolefin.

18. A composition according to claim 17 wherein the polyolefin is polypropylene.

19. A composition according to claim 16 wherein component (b) is N,N,N',N'-tetrakis(1-cyclohexyloxy-2,2,6,6-tetramethylpiperidin-4-yl) sebacamide.

20. A composition according to claim 16 wherein component (b) is N,N, N',N'-tetrakis(1-octyloxy-2,2,6,6-tetramethylpiperidin-4-yl)sebacamide.

21. A composition according to claim 16, wherein the polymer is a coating system based on alkyd, acrylic, acrylic-alkyd, polyester, epoxide, urethane, polyamide, vinyl or epoxy-polyester resins.

22. A composition according to claim 16 which contains a UV absorber or additional light stabilizer.

23. A method for stabilizing an synthetic polymer against oxidative, thermal or actinic degradation which comprises incorporating into said synthetic polymer an effective stabilizing amount of a compound according to claim 1.

* * * * *